United States Patent
Loebel et al.

(10) Patent No.: US 10,076,503 B2
(45) Date of Patent: Sep. 18, 2018

(54) DOSAGE OF DASOTRALINE AND METHOD FOR TREATMENT OF ADHD

(71) Applicant: SUNOVION PHARMACEUTICALS INC., Marlborough, MA (US)

(72) Inventors: Antony D. Loebel, Larchmont, NY (US); Kenneth S. Koblan, Brookline, MA (US)

(73) Assignee: SUNOVION PHARMACEUTICALS INC., Marlborough, MA (US)

( * ) Notice: Subject to any disclaimer, the term of this patent is extended or adjusted under 35 U.S.C. 154(b) by 0 days.

(21) Appl. No.: 15/310,351

(22) PCT Filed: May 12, 2015

(86) PCT No.: PCT/US2015/030357
§ 371 (c)(1),
(2) Date: Nov. 10, 2016

(87) PCT Pub. No.: WO2015/175523
PCT Pub. Date: Nov. 19, 2015

(65) Prior Publication Data
US 2017/0266134 A1    Sep. 21, 2017

Related U.S. Application Data

(60) Provisional application No. 61/992,619, filed on May 13, 2014.

(51) Int. Cl.
*A61K 31/135* (2006.01)
*A61K 9/00* (2006.01)

(52) U.S. Cl.
CPC .......... *A61K 31/135* (2013.01); *A61K 9/0053* (2013.01)

(58) Field of Classification Search
None
See application file for complete search history.

(56) References Cited

U.S. PATENT DOCUMENTS

2004/0092605 A1    5/2004   Jerussi et al.

FOREIGN PATENT DOCUMENTS

WO    2011/069032 A2    6/2011

OTHER PUBLICATIONS

International Search Report and Written Opinion issued in PCT/US20151030357, dated Jul. 28, 2015.
Koblan et al., "Dasotraline for the Treatment of Attention-Deficit/Hyperactivity Disorder: A Randomized, Double-Blind, Placebo-Controlled, Proof-of-Concept Trial in Adults," American Professional Society and Related Disorders Annual Meeting, Jan. 16-18, 2015; abstract 20, pp. 13-14.
Koblan et al., "Assessment of Human Abuse Potential of Dasotraline Compared to Methylphenidate and Placebo in Recreational Stimulant User," College on Problems of Drug Dependence (CCPD) 77th Annual Meeting, Jun. 13-18, 2015; abstract 327, p. 82.
Koblan et al., "Dasotraline for the Treatment of Attention-Deficit/Hyperactivity Disorder: A Randomized, Double-Blind, Placebo-Controlled, Proof-of-Concept Trial in Adults," Neuropsychopharmacology, Jun. 3, 2015; abstract p. 2, col. 2; p. 3, col. 2; pp. 4-6; p. 7, col. 2.
Extended Supplementary European Search Report and Communication issued in EP 15792455.6 dated Nov. 10, 2017.

*Primary Examiner* — Heidi L Reese
(74) *Attorney, Agent, or Firm* — Heslin Rothenberg Farley & Mesiti, P.C.

(57) ABSTRACT

Dosage forms and treatment regimens employing dasotraline for treating Attention Deficit Hyperactivity Disorder (ADHD) are disclosed. The compositions described herein exhibit no abuse potential.

3 Claims, 2 Drawing Sheets

DOSAGE OF DASOTRALINE AND METHOD FOR TREATMENT OF ADHD

CROSS-REFERENCE TO RELATED APPLICATIONS

This application is a national phase filing under 35 U.S.C. § 371 of PCT International Application PCT/US2015/30357, filed May 12, 2015. PCT/US2015/30357 claimed priority from U.S. provisional application 61/992,619, filed May 13, 2014. The entire contents of each of the prior applications are incorporated herein by reference.

FIELD OF THE INVENTION

The invention relates to dosage forms and treatment regimens employing [(1R,4S)-4-(3,4-dichlorophenyl)-1,2,3,4-tetrahydro-1-napthalenamine] (dasotraline) for treating Attention Deficit Hyperactivity Disorder (ADHD).

BACKGROUND OF THE INVENTION

Attention deficit hyperactivity disorder (ADHD) is a common condition that affects children and adolescents and can continue into adulthood for some. Although some experts believe that ADHD occurs in 8% to 10% of school-aged children, the National Institute of Mental Health (NIMH) estimates that 3% to 5% of children have ADHD. Considerable evidence suggests that about 50% of children may not outgrow ADHD. Whatever the exact figures, ADHD is a serious mental health problem in both children and adults.

Treatment for ADHD is most commonly in the form of stimulants such as methylphenidate (e.g. RITALIN®, CONCERTA®, METADATE®, METHYLIN®, DAYTRANA®, and QUILLIVANT®), amphetamine and dextroamphetamine (ADDERALL®, DEXEDRINE®) and prodrugs thereof (VYVANSE®). Although it may seem counterintuitive to treat hyperactivity with a stimulant, stimulants are thought to activate brain circuits that support attention and focused behavior, thus reducing hyperactivity. For many children, ADHD medications reduce hyperactivity and impulsivity and improve their ability to focus, work, and learn. Medications also may improve physical coordination. However, all the stimulants currently prescribed exhibit a high potential for abuse. All of the foregoing drugs are controlled by the DEA by its assignment of schedule II status, which means the drugs "have a high potential for abuse . . . and may lead to severe psychological and physical dependence."

Therefore, it would be advantageous to have a medication that could be given at in an oral dosage form at a dose that was effective in treating ADHD, but without the liability of abuse potential.

Trans 4-(3,4-dichlorophenyl)-1,2,3,4-tetrahydro-1-napthalenamine (which is also known as transnorsertraline or TNS) and its CNS pharmacology have been described in U.S. Pat. No. 7,105,699.

SUMMARY OF THE INVENTION

It has now been found that the (1R,4S) enantiomer of trans 4-(3,4-dichlorophenyl)-1,2,3,4-tetrahydro-1-napthalenamine, which will be referred to for convenience herein as "dasotraline", at a very specific dose and dose regimen, provides effective treatment of ADHD with no discernible abuse liability.

In one aspect, the invention relates to a method for treating ADHD while minimizing risk of substance abuse comprising administering to a patient diagnosed with ADHD an oral dosage form of dasotraline containing 4 mg of dasotraline.

In another aspect, the invention relates to a method for treating ADHD while minimizing risk of substance abuse comprising administering once daily to a patient diagnosed with ADHD an oral dosage form of dasotraline wherein the oral dosage form contains 4 mg of dasotraline.

DETAILED DESCRIPTION OF THE INVENTION

Figure 1:
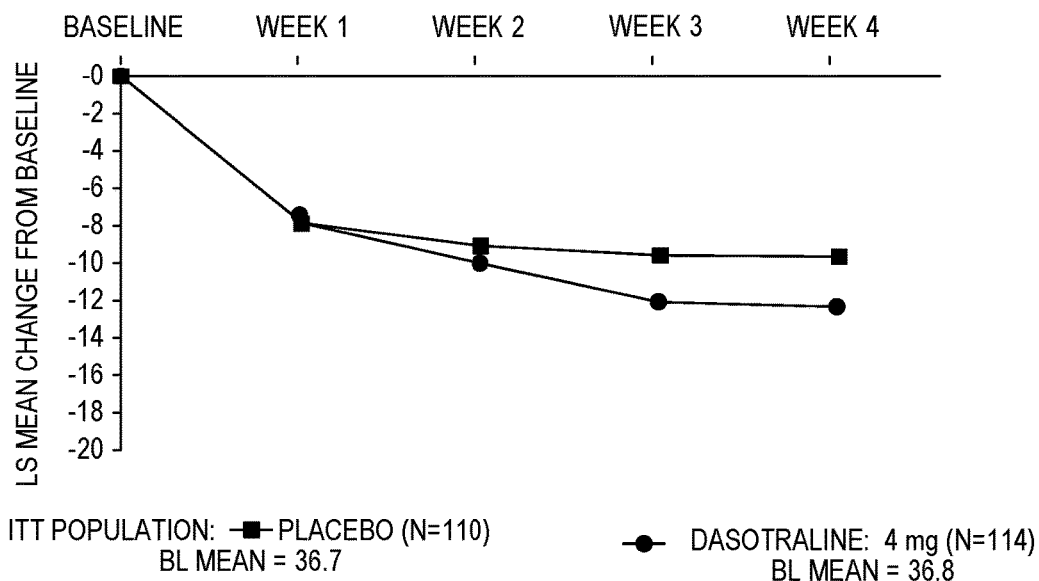
FIG. 1 is a graph of ADHD RS-IV total score least squares mean change from baseline as a function of time from initiation to week four for 4 mg dasotraline versus placebo.

Dasotraline [(1R,4S)-4-(3,4-Dichlorophenyl)-1,2,3,4-tetrahydronaphthalen-1-amine] is a novel compound with DNRI pharmacology. Dasotraline acts as a potent inhibitor of human DA transporters (DAT; dopamine uptake $IC_{50}$ 3 nM) and NE transporters (NET; norepinephrine uptake $IC_{50}$ 4 nM), and a weaker inhibitor of human serotonin transporters (SERT; serotonin uptake $IC_{50}$ 15 nM).

It has been found in a series of clinical trials, that dasotraline, when administered at 4 mg is both effective in treating ADHD and has no detectable abuse liability. Moreover, because of the combination of two peculiar features of dasotraline pharmacokinetics—namely an unusually long serum half-life coupled with a slow onset of dopamine transporter (DAT) inhibition—4 mg of dasotraline can be given once daily, and the dose doesn't have to be taken at any particular time each day, i.e. anytime-of-day dosing. The pharmacokinetic and pharmacodynamic characteristics of dasotraline suggest that it provides sustained, steady-state inhibition of DA and NE reuptake, which would address the hypothesized mechanisms underlying core deficits in the disorder In the studies described below, the efficacy of dasotraline in treating ADHD and its lack of abuse potential are shown in clinical trials in human patients. While not wishing to be held to current theory, a coherent explanation of this clinical outcome can be posited by comparison of dasotraline pharmacology to the pharmacology of conventional stimulants, and, in particular, to methylphenidate.

The proposed mechanism of action of methylphenidate, amphetamine and other stimulants is the release and increase of CNS dopamine. This release is secondary to its effect on the dopamine transport mechanism, which results in an increased amount of postsynaptic dopamine. The exact mechanism of action of methylphenidate is different from the amphetamines and cocaine, but the net effect of all three is an increase in synaptic dopamine. Radiographic studies with ($^{11}$C)-labeled methylphenidate and cocaine have found the binding of both drugs to be localized in the same brain region, the striatum. When methylphenidate is abused, it is the stimulation of D1 dopamine receptors in the nucleus accumbens and striato-orbitofrontal cortex that is thought to be related to the euphoria and repeated use.

Hoffman and Lefkowitz, in their chapter on catecholamines, sympathomimetic drugs, and adrenergic receptor antagonists in Goodman & Gilman's The Pharmacological Basis of Therapeutics, 9th edition state that the pharmacologic properties of methylphenidate "are essentially the same as those of the amphetamines" and warns of an abuse potential similar to that of the amphetamines, especially in patients with "a history of drug dependence or alcoholism."

Upon oral administration, methylphenidate is rapidly and completely absorbed from the gastrointestinal tract. Peak concentrations occur 1 to 2 hours after dose administration. The pharmacokinetic half-life of methylphenidate is approximately 2 hours. When methylphenidate and cocaine are administered intravenously, their pharmacokinetics are quite similar—the percentage of each drug taken up by the brain and their rates of uptake are parallel, although the clearance from the brain of cocaine is faster than that of methylphenidate. The receptor-binding affinities for cocaine and methylphenidate are similar at the dopamine transporter in the basal ganglia and the striatum. Notably, the "high" associated with intravenous methylphenidate occurs before peak concentrations appear in the basal ganglia. Thus it appears that abuse may be related to a rapid surge in dopamine levels in the striatum. Against this background, the lack of abuse potential of dasotraline would be consistent with its pharmacokinetic profile. Dasotraline exhibits a time-to-maximum-concentration ($t_{max}$) of about 10-12 hours (compared to methylphenidate's 1-2 hours) and a serum half-life ($t_{1/2}$) of 47-77 hours. The consequence of the slow increase in dopamine is the absence of a "high", and the consequence of the long $T_{1/2}$ is that serum concentration gradually increases to a steady state. Thus if the dose of dasotraline administered orally is a 4 mg dose, it will provide effective therapy without inducing a high.

Clinical results set forth below indicate that an oral dosage form containing 4 mg of dasotraline will provide statistically significant improvement in ADHD after about two to three weeks of administration. The advantage of a dose of 4 mg is that it produces an ultimately efficacious serum concentration while, at the same time, minimizing the likelihood of side effects and exhibiting no drug-liking response in human test subjects.

In the studies below, dasotraline was administered as its hydrochloride salt. In addition to administration as the free base, dasotraline may also be formulated as a pharmaceutically acceptable salt other than the hydrochloride. The term "pharmaceutically acceptable salt" refers to salts whose counter ion derives from pharmaceutically acceptable non-toxic acids and bases. Suitable pharmaceutically acceptable acids for salts of the compounds of the present invention include, for example, acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. Dasotraline hydrochloride is a preferred salt, and its preparation and formulation are described in US published application 2013/0116332. The amounts described herein are the amount of dasotraline calculated as the free base. The amounts can be adjusted according to the salt form of dasotraline being employed in the formulation, and, indeed, in the clinical studies described below, an amount of hydrochloride salt equivalent to 4 mg of free dasotraline was employed.

Formulations of the present invention suitable for oral administration may be presented as discrete units such as capsules, cachets or tablets each containing 4 mg of dasotraline or a salt containing the equivalent of 4 mg of dasotraline free base. It should be understood that formulations of this invention may include other agents conventional in the art having regard to oral formulations, for example colorants, disintegrants and flavoring agents.

As used herein, "treatment" or "treating," or "palliating" or "ameliorating" are used interchangeably herein. These terms refers to an approach for obtaining a therapeutic benefit with the eradication or amelioration of one or more of the symptoms associated with ADHD such that an improvement is observed in the patient, notwithstanding that the patient may still be afflicted with the ADHD. The compositions may be administered to a patient diagnosed with ADHD, whether by a physician, physician's assistant, nurse or other healthcare professional.

A Phase 2, randomized, double-blind, parallel-group, multicenter, outpatient study evaluated the efficacy and safety of dasotraline in adults with ADHD using 4 mg once daily versus placebo over a 4-week treatment period. The study consisted of three periods including Screening, Treatment, and Washout/Follow-up, as described below. Efficacy was evaluated using the ADHD Rating Scale Version IV (ADHD RS-IV) with adult prompts. Effects on cognition were evaluated using the clinical data repository system. Safety and tolerability were monitored throughout the study by collection of physical examinations, 12-lead electrocardiograms (ECG), vital signs, adverse events (AEs), hematology, blood chemistry, urinalysis, Insomnia Severity Index (ISI), and Columbia—Suicide Severity Rating Scale (C-SSRS). Population pharmacokinetic methodology was performed using the measured plasma dasotraline concentrations.

All subjects had an ADHD RS-IV Score≥26 and a CGI-S score≥4 at Baseline (Day 1). On Day 1, subjects were randomized via the interactive response system into either a treatment group (4 mg dasotraline) or placebo, and began taking study drug that night before going to bed. Subjects self-administered the study drug at home on Days 1 through 28, at approximately the same time each night. After Day 1 subjects returned to the clinic on Days 8, 15, 22, and 29. Beginning at Day 1 and at every visit during the treatment period, the ADHD RS-IV, Wender-Reimherr Adult Attention Deficit Disorder Scale (WRAADDS), and clinical global impression—severity (CGI-S) were completed. The clinical data repository system was administered at Baseline, and Days 15 and 29. Blood draws for dasotraline plasma concentrations were collected on Days 1, 8, 15, 22, and 29.

At the end of the 4-week treatment period (Day 29), medication was abruptly discontinued, and subjects entered a 2-week washout period to monitor dasotraline plasma concentrations during washout, evaluate the occurrence of withdrawal symptoms using the Physician Withdrawal Checklist, and determine the duration of treatment effect after the cessation of study drug. At Days 36 and 43, subjects returned to the clinic and the ADHD RS-IV, WRAADDS, and CGI-S were completed. The clinical data repository system was completed on Day 43.

Figure 2:
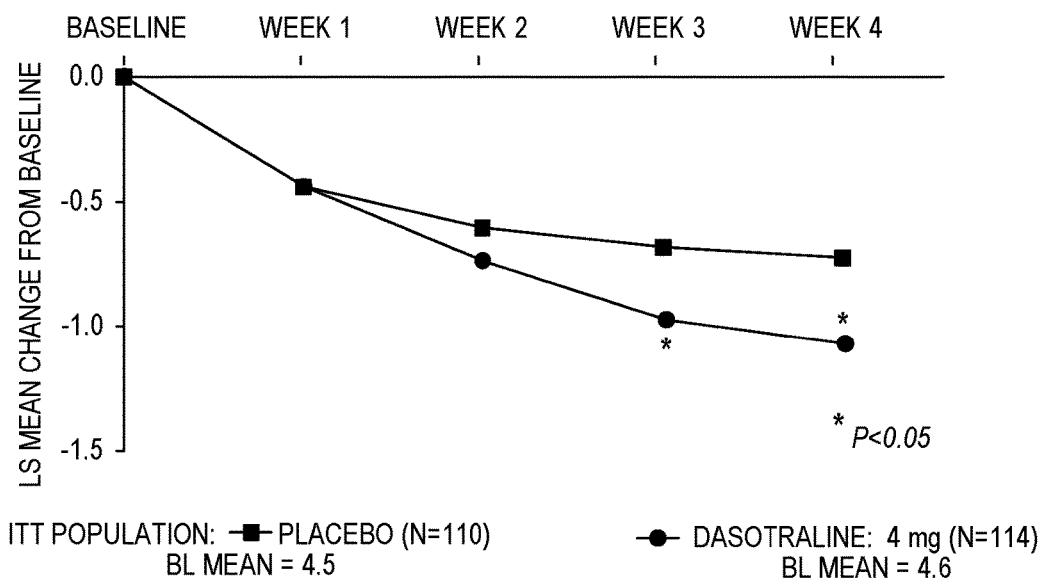
FIG. 2 is a graph of least squares mean change from baseline as a function of time from initiation to week four for 4 mg dasotraline versus placebo based on CGI-S score.

The results are presented graphically in FIGS. 1 and 2. FIG. 1 is a graph of least squares mean change from baseline as a function of time from initiation to week four for 4 mg dasotraline versus placebo based on ADHD RS-IV total score. FIG. 2 is a graph of LS mean change from baseline as a function of time from initiation to week four for 4 mg dasotraline versus placebo based on CGI-S score. The difference is statistically different at weeks three and four ($p<0.05$). The Wender-Reimherr ADD total score did not improve enough to achieve statistical significance, but the subscore for the attention difficulties component showed statistically significant improvement at week 4 for the dasotraline group vs the placebo group.

On the computerized cognitive assessment battery, no significant main effects for dasotraline were observed for measures of attention, working memory, or episodic memory. Treatment-emergent adverse events (TEAEs) were higher than the percentage of TEAEs in the placebo group. The majority of adverse events were rated as mild or moderate; the incidence of events rated as severe was 6% in the dasotraline group and 2.7% in the placebo group. The most common adverse events leading to discontinuation (and occurring≥2 patients) in the dasotraline group were insomnia (2.6%) and anxiety (2.6%).

Figure 3:
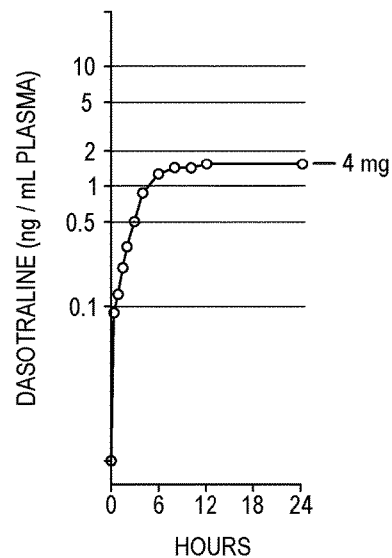
FIG. 3 is a graph of serum concentration of dasotraline in ng/mL as a function of time

When serum concentration of dasotraline in ng/mL was examined as a function of time, it was seen that the serum concentration began to plateau by week four. In the course of earlier studies, it was observed that a single dose of 4 mg of dasotraline produced a maximum serum concentration ($C_{max}$) of about 1.5 ng/mL, which was achieved very slowly ($t_{max}>6$ hours) and without any "spike". FIG. 3 is a graph of dasotraline concentration (in ng/mL) as a function of time, following a single administration.

From other studies (not shown) it was found that 50% DAT site occupancy was achieved at about 5-6 ng/mL, i.e. dasotraline does not achieve a concentration sufficient to occupy 50-75% of DAT sites on a single administration. Thus, from the clinical trial it can be seen that a 4 mg dosage form can reach therapeutic efficacy after two weeks of once-a-day administration, and from the serum concentration study it can be seen that it will do so without a spike in DAT occupancy. In the present study, dasotraline 4 mg/d resulted in mean concentrations at steady state of 6 ng/mL. Dasotraline 4 mg/d also decreased circulating DHPG levels, indicative of central inhibition of norepinephrine transporters. The DNRI mechanism distinguishes dasotraline from atomoxetine, a nonstimulant which inhibits only norepinephrine transporters. The slow absorption and long elimination half-life of dasotraline contrasts with the pharmacokinetics of amphetamine, methylphenidate and atomoxetine. It is also possible to use the 4 mg dosage form as member of a series of dosages such that one could dose-titrate upward or downward, either from a 4 mg dose to a 5, 6, 7 or 8 mg dose, or from an initial loading dose of 6, 7 or 8 mg to a maintenance dose of 4 mg. For example, one could dose at 4 mg/day for a period of days, then 6 mg/day for a period of days and finally at 8 mg/day, or vice versa. One could also titrate up from or down to 2 mg.

Since the abuse potential of methylphenidate and similar DAT inhibitors is believed to be associated with rapid occupation of DAT sites, a study of dasotraline was undertaken to see if it would be free of the abuse liability associated with other stimulants.

A single-dose, randomized, double-blind, double-dummy, placebo- and active-controlled crossover study with 6 Treatment Visits per subject was undertaken. The abuse potential of three doses of dasotraline (8 mg, 16 mg, and 36 mg) was compared to that of placebo, and 40 mg and 80 mg methylphenidate (positive control) in healthy recreational stimulant users. Subjects participated in a medical screening visit (Visit 1), one 4-day inpatient qualification phase (Visit 2), a treatment phase (Visits 3 to 8) consisting of six 5-day inpatient treatment visits, and a safety follow-up visit (Visit 9). Within 21 days of the screening visit, subjects were enrolled and attended a qualification phase in which they received either 60 mg methylphenidate or matching placebo in a randomized double-blind crossover manner. Dosing times were separated by approximately 24 hours to ensure that subjects could discriminate and show positive effects of the positive control.

Healthy female and male subjects aged 18 to 55 years (inclusive), who were recreational central nervous system (CNS) stimulant users with cocaine experience and who had passed the methylphenidate qualification phase, were randomized into the treatment.

Drug administration occurred on Day 1 of each treatment visit followed by pharmacodynamic (PD), pharmacokinetic (PK), and safety assessments conducted for up to 72 hours post-dose. Subjects received each of the following 6 treatments in a randomized, double-blinded, double-dummy fashion (one per treatment visit): 8 mg dasotraline, 16 mg dasotraline, 36 mg dasotraline, 40 mg methylphenidate, 80 mg methylphenidate or placebo. Subjects were randomized to one of 6 treatment sequences according to a 6×6 William square design. The capsules received at each treatment visit (Visits 3 to 8) were identical. Serial pharmacodynamic and pharmacokinetic evaluations were taken at each treatment visit. Pharmacokinetic analysis was performed for dasotraline. Safety monitoring included regular assessments of vital signs, clinical laboratory tests, and adverse events (AEs), as well as continuous telemetry monitoring for at least 12 hours post-dose. Treatment visits were separated by a washout interval of at least 21 days (from the day of dosing). Subjects returned for the safety follow-up visit within approximately 14 days following the end of the last treatment visit.

Figure 4:
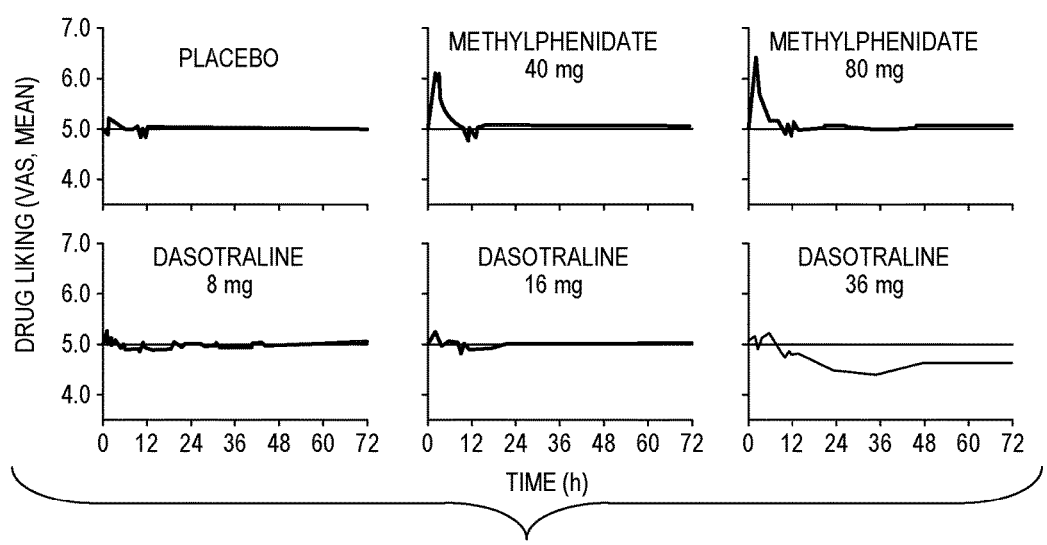
FIG. 4 depicts 6 side-by-side comparisons of drug-liking for placebo, methylphenidate at two doses and dasotraline at three doses on graphs of a measure of liking vs time. On these graphs, 50% represents neutrality.

Thirty-five subjects completed the study, which, based on post-hoc power calculations, still resulted in greater than 90% power to detect a difference in means between placebo and methylphenidate. The effects of the positive control, methylphenidate, were consistent with a stimulant drug with abuse potential, as significant differences compared to placebo were observed on the majority of pharmacodynamic endpoints, including the primary measure of Drug Liking Visual Analog Scale. Consistent with these results, methylphenidate was associated with strong stimulant effects, as measured by secondary stimulant measures, and methylphenidate was strongly identified as a stimulant (e.g., d-amphetamine, methamphetamine, or cocaine) and strongly identified as not placebo on the Drug Similarity Visual Analog Scale. These results demonstrate that the study was valid and that the subjects and measures were sensitive for evaluating the abuse-related effects of stimulant drugs. Methylphenidate was "liked" by subjects overall, subjects were willing to take methylphenidate again, and would be willing to pay more for methylphenidate compared to placebo. On the other hand, on most pharmacodynamic endpoints, the effects of dasotraline were not significantly different from those of placebo, and the 8 mg dose showed a similar profile to placebo across all pharmacodynamic endpoints. Thus, patients taking therapeutic doses of dasotraline or abusers initially experimenting with single tablet or capsules should not experience abuse-related subjective effects. Even at 16 mg, there were very few statistically significant differences from placebo. The results are shown graphically in FIG. 4, which compares drug-liking for placebo, methylphenidate at two doses and dasotraline at three doses.

The foregoing studies demonstrate that a single 4 mg oral dose of dasotraline, given once daily, provides efficacy in treating ADHD while avoiding abuse potential.

Four mg capsules and placebo were prepared with the following composition:

Amount (mg/cap)

|  | Placebo | 4 mg |
|---|---|---|
| dasotraline hydrochloride | 0 | 4.5 |
| Talc | 2.5 | 5 |
| Pearlitol 160C | 146.3 | 139.3 |
| Sodium startch glycolate | 9.6 | 9.6 |
| Magnesium Stearate | 1.6 | 1.6 |
| Total wt (mg) | 160 | 160 |

The following are additional aspects of the invention:

A method for treating ADHD while minimizing risk of substance abuse comprising administering to a patient diagnosed with ADHD an oral dosage form of dasotraline wherein said oral dosage form contains 4 mg of dasotraline.

A method for treating ADHD comprising commencing treatment by orally administering to a subject in need of such treatment, on a single day, a first dose in the form of a tablet or capsule, wherein said tablet or capsule comprises 4 mg of dasotraline and continuing said treatment by orally administering, once daily, a tablet or capsule comprising 4 mg of dasotraline.

A tablet or capsule comprising 4.5 mg of dasotraline hydrochloride and one or more pharmaceutical excipients.

The invention claimed is:

1. A method for treating ADHD while minimizing risk of substance abuse comprising administering once daily to a patient diagnosed with ADHD an oral dosage form of dasotraline wherein said oral dosage form contains 4 mg of dasotraline.

2. A method according to claim 1 wherein said oral dosage form contains 4 mg of dasotraline in the form of its hydrochloride salt.

3. A method according to claim 1 wherein said dosage form consists of 4.5 mg of dasotraline hydrochloride and one or more pharmaceutically acceptable excipients.

* * * * *